United States Patent [19]

Meyer et al.

[11] Patent Number: 4,497,647
[45] Date of Patent: Feb. 5, 1985

[54] TRIAZOLYLALKENES AS FUNGICIDES AND PLANT GROWTH REGULANTS

[75] Inventors: Alfred Meyer, Basel; Walter Kunz, Oberwil; Ludwig Maier, Arlesheim; Hermann Rempfler, Ettingen, all of Switzerland

[73] Assignee: Ciba-Geigy Corporation, Ardsley, N.Y.

[21] Appl. No.: 466,825

[22] Filed: Feb. 16, 1983

[30] Foreign Application Priority Data

Feb. 19, 1982 [CH] Switzerland ............... 1049/82

[51] Int. Cl.³ ............... A01N 43/50; A01N 43/64; C07D 233/60; C07D 249/08
[52] U.S. Cl. ............... 71/76; 71/78; 71/92; 71/77; 548/101; 548/112; 548/262; 548/335; 548/341; 514/184; 514/383; 514/189; 514/191
[58] Field of Search ............... 542/400, 429, 413, 426, 542/468; 548/101, 262, 335, 341; 424/245, 269, 273 R; 71/78, 76, 92

[56] References Cited

FOREIGN PATENT DOCUMENTS 0047057 3/1982 European Pat. Off. ............ 548/262
2076402 12/1981 United Kingdom ............... 548/338

Primary Examiner—Alton D. Rollins
Attorney, Agent, or Firm—Frederick H. Rabin

[57] ABSTRACT

The invention relates to novel azolyl-olefin derivatives of the general formula I $$R_2-\underset{\underset{R_3}{|}}{C}=CH-R_1, \quad (I)$$

wherein
$R_1$ is an azolyl group,
$R_2$ is $C_1$-$C_{12}$alkyl, $C_3$-$C_8$cycloalkyl, $C_1$-$C_4$alkyl substituted by unsubstituted or substituted phenyl, $C_1$-$C_4$alkoxycarbonyl or $C_2$-$C_6$alkenyl, or is $C_3$-$C_8$cycloalkyl which is substituted by 1 to 4 $C_1$-$C_4$alkyl groups,
$R_3$ is $C_1$-$C_{12}$alkyl, $C_3$-$C_8$cycloalkyl which is substituted by 1 to 4 $C_1$-$C_4$alkyl groups, or is the —C($R_4$)($R_5$)—[CH($R_4$)]$_n$—X—$R_6$ group, wherein n is 0 or 1 and $R_4$ and $R_5$, each independently of the other, are hydrogen or $C_1$-$C_4$alkyl,
X is oxygen or sulfur,
$R_6$ is a radical selected from the group consisting of $C_1$-$C_8$alkyl, $C_3$-$C_8$cycloalkyl, $C_3$-$C_6$alkenyl, $C_3$-$C_6$alkynyl, phenyl, naphthyl, biphenyl, benzylphenyl, benzoxyphenyl, phenoxyphenyl and aralkyl, which radical is substituted by one or more of halogen, cyano, $C_1$-$C_4$alkyl, $C_1$-$C_5$alkoxy, $C_1$-$C_5$haloalkoxy, $C_1$-$C_3$alkylthio, $C_1$-$C_3$haloalkyl, $C_1$-$C_3$haloalkylthio, nitro, —COOR$_7$ or —CON($R_8$)($R_9$), wherein $R_7$ is $C_1$-$C_4$alkyl and
$R_8$ and $R_9$, each independently of the other, are hydrogen or $C_1$-$C_4$alkyl, and the acid addition salts quaternary azolium salts and metal complexes thereof.

The invention also describes methods of preparing these compounds as well as agrochemical compositions which contain one of said compounds as active ingredient. The invention further describes a method of controlling phytopathogenic microorganisms and/or of regulating plant growth which comprises the use of the novel compounds.

9 Claims, No Drawings

TRIAZOLYLALKENES AS FUNGICIDES AND PLANT GROWTH REGULANTS

The present invention relates to novel substituted azolyl-olefin derivatives of the formula 1 below, and to the acid addition salts, quaternary azolium salts and metal complexes thereof. The invention relates also to the preparation of these compounds and to microbicidal and growth-regulating compositions which contain at least one of these compounds as active ingredient. The invention relates further to the preparation of said compositions and to the use of the novel compounds or compositions for controlling plant growth and for controlling harmful microorganisms.

The present invention accordingly provides compounds of the general formula I

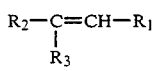  (I)

wherein
$R_1$ is an azolyl group,
$R_2$ is $C_1$–$C_{12}$alkyl, $C_3$–$C_8$cycloalkyl, $C_1$–$C_4$alkyl substituted by unsubstituted or substituted phenyl, $C_1$–$C_4$alkoxycarbonyl or $C_2$–$C_6$-alkenyl, or is $C_3$–$C_8$cycloalkyl which is substituted by 1 to 4 $C_1$–$C_4$alkyl groups,
$R_3$ is $C_1$–$C_{12}$alkyl, $C_3$–$C_8$cycloalkyl which is substituted by 1 to 4 $C_1$–$C_4$alkyl groups, or is the —C($R_4$)($R_5$)—[CH($R_4$)]$_n$—X—$R_6$ group, wherein n is 0 or 1 and $R_4$ and $R_5$, each independently of the other, are hydrogen or $C_1$–$C_4$alkyl,
X is oxygen or sulfur,
$R_6$ is a radical selected from the group consisting of $C_1$–$C_8$alkyl, $C_3$–$C_8$cycloalkyl, $C_3$–$C_6$alkenyl, $C_3$–$C_6$alkynyl, phenyl, naphthyl, biphenyl, benzylphenyl, benzoxyphenyl, phenoxyphenyl and aralkyl, which radical is substituted by one or more of halogen, cyano, $C_1$–$C_4$alkyl, $C_1$–$C_5$alkoxy, $C_1$–$C_5$haloalkoxy, $C_1$–$C_3$alkylthio, $C_1$–$C_3$-haloalkyl, $C_1$–$C_3$haloalkylthio, nitro, —COO$R_7$ or —CON($R_8$)($R_9$), wherein $R_7$ is $C_1$–$C_4$alkyl and
$R_8$ and $R_9$, each independently of the other, are hydrogen or $C_1$–$C_4$alkyl, and the acid addition salts, quaternary azolium salts and metal complexes thereof.

The term azolyl denotes a 5-membered heterocyclic ring containing nitrogen as heteroatom and having aromatic character. Typical representatives are 1H-1,2,4-triazole, 4H-1,2,4-triazole and 1H-imidazole. Depending on the indicated number of carbon atoms, alkyl by itself or as moiety of another substituent comprises e.g. the following groups: methyl, ethyl, propyl, butyl, pentyl, hexyl, heptyl, octyl, nonyl, decyl, undecyl, dodecyl etc., and the isomers thereof, e.g. isopropyl, isobutyl, tert-butyl, isopentyl etc. Haloalkyl is a trihalogenated to perhalogenated alkyl substituent, e.g. $CHCl_2$, $CF_3$, $CHF_2$, $CH_2Cl$, $CCl_3$, $CH_2F$, $CH_2CH_2Cl$, $CHBr_2$, etc. Throughout this specification, halogen denotes fluorine, chlorine, bromine or iodine, with fluorine, chlorine or bromine being preferred. Naphthyl is α- or β-naphthyl, with α-naphthyl being preferred. Haloalkoxy or haloalkylthio denotes an alkoxythio or alkylthio radical respectively whose haloalkyl moiety is as defined above for haloalkyl. Alkenyl is e.g. propen-1-yl, allyl, buten-1-yl, buten-2-yl or buten-3-yl. Alkynyl is e.g. propion-1-yl or propargyl. Aryl is e.g. naphthyl, especially phenyl; and aralkyl is a lower alkyl radical which is substituted by one of the above aryl groups. Depending on the indicated number of carbon atoms, cycloalkyl is e.g. cyclopropyl, cyclobutyl, cyclopentyl, cyclohexyl, cycloheptyl, cyclooctyl etc.

Accordingly, the present invention relates to the free compounds of the formula I and to the acid addition salts, quaternary azolium salts and metal complexes thereof. The free compounds are preferred.

Examples of salt-forming acids are inorganic acids, e.g. hydrohalic acids such as hydrofluoric acid, hydrochloric acid, hydrobromic acid or hydriodic acid, and also sulfuric acid, phosphoric acid, phosphorous acid, nitric acid; and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Metal complexes of the formula I consist of the basic organic molecule and an inorganic or organic metal salt, for example the halides, nitrates, sulfates, phosphates, acetates, trifluoroacetates, trichloroacetates, propionates, tartrates, sulfonates, salicylates, benzoates etc. of the elements of the third and fourth main group of the Periodic Table such as aluminium, tin or lead, and of the first to eighth auxiliary group such as chromium, manganese, iron, cobalt, nickel, copper, zinc, silver, mercury etc. Preferred elements are those of the auxiliary groups of the fourth period. The metals may exist in different valency states. The metal complexes of the formula I may be mononuclear or polynuclear, i.e. they can contain one or more parts of the organic molecule as ligands. Complexes with copper, zinc, manganese and tin are preferred.

The compounds of formula I are oils, resins or mainly solids which are stable at room temperature and have very valuable microbicidal and growth regulating properties. They can be used in agriculture or related fields preventively and curatively for controlling phytopathological microorganisms and for regulating plant growth, for which utility the triazolylmethyl derivatives falling within the scope of formula I are preferred. The compounds of formula I are very well tolerated by cultivated plants.

On account of their pronounced growth regulating and/or microbicidal properties, the following groups of compounds are preferred:

(a) Compounds of formula I, wherein $R_1$ is 1H-1,2,4-triazole; $R_2$ is $C_1$–$C_9$alkyl; $R_3$ is the —C($R_4$)($R_5$)—X—$R_6$ group, in which $R_4$ and $R_5$ independently of the other are hydrogen or $C_1$–$C_4$alkyl; X is oxygen and $R_6$ is $C_1$–$C_3$alkyl, phenyl or phenyl which is substituted by halogen, $CF_3$ or $C_1$–$C_3$alkyl.

(b) Compounds of the formula I, wherein $R_1$ is 1H-1,2,4-triazole; $R_2$ is tert-butyl or isopropyl; $R_3$ is the —C($R_4$)($R_5$)—X—$R_6$ group, wherein $R_4$ is hydrogen and $R_5$ is $C_1$–$C_4$alkyl, X is oxygen and $R_6$ is methyl, phenyl or phenyl which is substituted by chlorine, bromine, fluorine, $CF_3$ or methyl.

The following individual compounds are particularly preferred:
1-(1H-1,2,4-triazol-1-yl)-2-(4-chlorophenoxymethyl)-3,3-dimethylbutene, 1-(1H-1,2,4-triazol-1-yl)-2-isopropyl-3-(4-chloro-phenoxy)-pentene,
1-(1H-1,2,4-triazol-1-yl)-2-(tert-butyl)-3-(4-chloro-phenoxy)-heptene,
1-(1H-1,2,4-triazol-1-yl)-2-(tert-butyl)-3-(4-fluoro-phenoxy)-butene,
in the form of their mixtures of isomers and of pure E- or Z-isomers.

The compounds of formula I may be prepared by a number of reaction variants (i) to (iv) as illustrated below in a reaction scheme and subsequently discussed in detail. In formulae I, II, III, IV, V, VI, VII, VIII, IX, X, XI, XII, XIII, XIV and XV, the substituents $R_1$, $R_2$ and $R_3$ are as defined for formula I. $R_{10}$ is phenyl or $C_1$-$C_4$alkyl, $R_{11}$ is phenyl or $C_1$-$C_4$alkyl which is unsubstituted or substituted by hydroxyl, A is one of the customary leaving groups, viz. chlorine, bromine, iodine or the groups —OCO—$R_{12}$ or —OSO—$R_{12}$, in which $R_{12}$ is $C_1$-$C_3$alkyl, $C_1$-$C_3$haloalkyl, phenyl or phenyl substituted by halogen, methyl, nitro, trifluoromethyl or methoxy, but is preferably chlorine or bromine. The term "Hal" denotes halogen, preferably fluorine, chlorine or bromine. M is an alkali metal atom, preferably sodium or potassium.

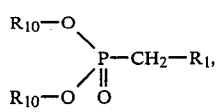

wherein $R_2$ and $R_3$ are as defined for formula I, with a 1H-azol-1-yl-methylphosphonate of the formula III

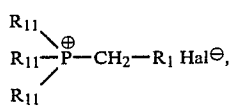

wherein each of the radicals $R_{10}$ independently of the other is phenyl or $C_1$-$C_4$alkyl and $R_1$ is an azolyl group, or with a phosphonium salt of the formula IV

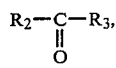

wherein each of the radicals $R_{11}$ independently of the other is phenyl or $C_1$-$C_4$alkyl which is unsubstituted or substituted by hydroxyl, $R_1$ is an azolyl group, and Hal is chlorine or bromine, in an inert solvent and in the presence of a strong base.

REACTION-SCHEME

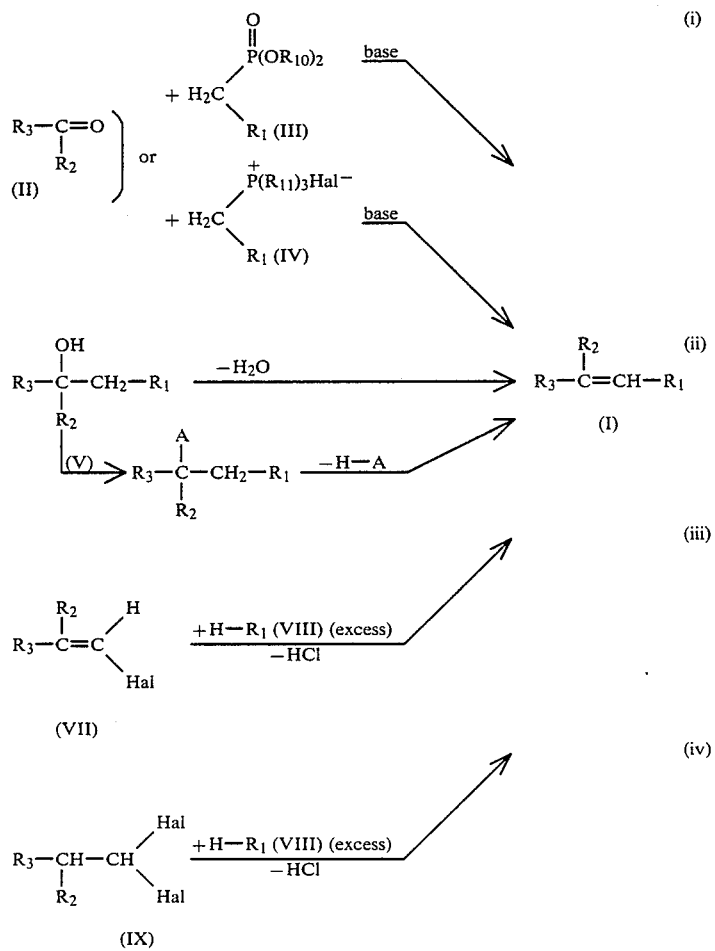

In detail, the compounds of the formula I may be prepared as follows:

(i) Azolyl-olefin derivatives of the formula I may be prepared by reacting a ketone of the formula II The conversion of the ketone of the formula II into the azolyl-olefin derivative of the formula I can thus be carried out by the process variant either using the phosphonate of the formula III or the phosphonium salt of the formula IV.

The variant using as reactant the phosphonate of the formula III is conveniently carried out by reacting the phosphonate first with a strong base and then with the ketone of the formula II.

Suitable solvents for this reaction are inert, polar aprotic solvents. Examples of such solvents are ethers such as diethyl ether, tetrahydrofuran, dioxan, dimethoxyethane or diethylene glycol dimethyl ether; acid amides such as dimethylformamide, 2-pyrrolidinone or hexamethylphosphoric triamide; and sulfoxides such as dimethylsulfoxide.

Preferred solvents are those having a boiling point above 60° C., e.g. tetrahydrofuran, dioxan, dimethoxyethane, dimethylformamide or dimethylsulfoxide.

Suitable strong bases are: organometallic compounds such as methyllithium, propyllithium, butyllithium, phenyllithium or sodium triphenylmethane; alcoholates such as sodium methylate, sodium ethylate, potassium ethylate or potassium tert-butylate; metal hydrides such as lithium hydride, sodium hydride or calcium hydride; and alkali amides such as sodium amide or lithium diisopropylamide.

Preferred bases are the metal hydrides, the organometallic compounds and the alcoholates.

As both the reaction of the phosphonate III with the strong base to give the corresponding salt and the further reaction with the ketone II are exothermic, the reaction vessel is always cooled before the addition of reagent and then heated to bring the reaction to completion. Suitable temperature ranges are, for the first step, from −40° to +40° C., preferably from −20° to +40° C., and, for the second step, from −20° to +80° C., preferably from 0° to 60° C. However, it is also possible to charge the reaction vessel with the base at 0° to 60° C. and then to add the mixture of ketone(II) and phosphonate(III).

The azolyl-olefin derivative of the formula I so obtained is isolated by adding water to the reaction mixture, extracting the reaction mixture with a water-immiscible solvent, and concentrating the organic phases.

The variant using the phosphonium salt of the formula IV as reactant is conveniently carried out such that the phosphonium salt is treated first with a strong base and then reacted with the ketone of the formula II.

It has also been found advantageous in this reaction to add an excess of base. The excess will normally be less than twice the molar amount required for the reaction, i.e. from 0.01 to 1 equivalent.

Suitable solvents for this reaction are inert, polar aprotic solvents. Examples of such solvents are diethyl ether, tetrahydrofuran, dioxan, dimethoxyethane of diethylene glycol dimethyl ether; acid amides such as dimethylformamide, 2-pyrrolidinone or hexamethylphosphoric triamide; and sulfoxides such as dimethylsulfoxide.

Preferred solvents are those having a boiling point above 80° C., e.g. dioxan, dimethoxyethane, diethylene glycol dimethyl ether, dimethylformamide, 2-pyrrolidinone or dimethylsulfoxide.

Suitable strong bases are: organometallic compounds such as methyllithium, propyllithium, butyllithium, phenyllithium or sodium triphenylmethane; alcoholates such as sodium methylate, sodium ethylate, potassium methylate or potassium tert-butylene; metal hydrides such as lithium hydride, sodium hydride or calcium hydride; and alkali amides such as sodium amide or lithium diisopropylamide.

Preferred bases are the metal hydrides and the organometallic compounds.

As both the reaction of the phosphonium salt with the strong base to give the corresponding ylide and the further reaction with the ketone II are exothermic, the reaction vessel is always cooled before the addition of reactant and then heated to bring the reaction to completion. Suitable temperature ranges are, for the first step, from −40° to +80° C., preferably from −20° to +40° C., and, for the second step, from −20° to +110° C., preferably from 0° to 60° C.

The azolyl-olefin derivative of the formula I is isolated by diluting the reaction mixture with diethyl ether, isolating the precipitated phosphine oxide by filtration, and concentrating the filtrate. In order to obtain product adhering to the phosphine oxide it may be necessary to wash the filter cake repeatedly with ether.

Where salts of the formula III or IV are used as starting materials in process variant (i) it can be very advantageous to add a crown ether. For example, the use of [18]-crown-6 or of [15]-crown-5 is very advantageous.

In process variant (i) there are normally obtained mixtures of cis- and trans-olefins in which the cis-olefin isomer generally predominates. The formation of a higher trans-olefin isomer can be effected by means of a larger excess of ylide or by addition of lithium salts (e.g. LiClO4) [cf. M. Schlosser, Chem. Ber. 103. 2841].

The individual isomers (cis- and trans-olefins) may also be separated by conventional physical methods (e.g. chromatography) and exhibit different biological activity.

(ii) Azolyl-olefin derivatives of formula I can further be prepared by removing water either direct from a compound of the formula V

wherein $R_1$, $R_2$ and $R_3$ are as defined for formula I, with a condensing agent, or by conveniently converting the compound of the formula V first into a compound of the formula VI

by replacing the free hydroxyl group by a customary leaving group A, and then converting said compound VI into a final product of the formula I by removal of H-A. Within the scope of this invention, a customary leaving group A will be understood as meaning the substituents chlorine, bromine, iodine as well as the groups —OCO—$R_{12}$ and —OSO—$R_{12}$, where $R_{12}$ is $C_1$-$C_3$alkyl, $C_1$-$C_3$haloalkyl, phenyl or phenyl substituted by halogen, methyl, nitro, trifluormethyl or methoxy, but is preferably chlorine or bromine.

The reaction can often be carried out continuously in the same reaction vessel, i.e. although the intermediate of the formula VI can be isolated from the reaction medium, it need not be.

The removal of water from compounds of the formula V is conveniently effected in a conventional inert solvent or mixture of solvents. Examples of suitable solvents are alcohols such as lower alkanols (methanol, ethanol, n-propanol, isopropanol, n-butanol, amyl alcohol etc.); ethers and ethereal compounds such as dialkyl ethers (diethyl ether, diisopropyl ether, tert-butylmethyl ether etc.), anisole, dioxan, tetrahydrofuran; aliphatic and aromatic hydrocarbons such as benzene, toluene, xylene, petroleum ether; halogenated hydrocarbons such as chlorobenzene, methylene chloride, ethylene chloride, chloroform, carbon tetrachloride, tetrachloroethylene etc. Suitable condensing agents are e.g. strong acids, especially concentrated or diluted mineral acids such as phosphoric acid, sulfuric acid or hydrohalic acids (hydrochloric, hydrobromic, hydriodic or hydrofluoric acid). The reaction is carried out in the temperature range from 0° to 180° C., usually at elevated temperature. As condensing agent it is also possible to use a carbodiimide such as N,N'-dicyclohexylcarbodiimide, in which case the reaction temperature is in the range from 0° to 150° C.

The replacement of the free hydroxyl group in the compounds of formula V by a leaving group A is preferrably carried out in an inert solvent. Examples of such solvents are: aromatic and aliphatic hydrocarbons such as benzene, toluene, xylenes, petroleum ether, ligroin or cyclohexane; halogenated hydrocarbons such as chlorobenzene, methylene chloride, ethylene chloride, chloroform, carbon tetrachloride or tetrachloroethylene; ethers and ethereal compounds such as diethyl ether, diisopropyl ether, tert-butylmethyl ether, dimethoxyethane, dioxan, tetrahydrofuran or anisole; esters such as ethyl acetate, propyl acetate or butyl acetate; nitriles such as acetonitrile; or compounds such as dimethylsulfoxide, dimethylformamide and mixtures of such solvents.

The introduction of the leaving group A is effected by conventional methods. If A is chlorine or bromine, then phosphoroxy chloride, phosphorus trichloride, phosphorus pentachloride or, preferably, thionyl chloride, may be used as reagent. The reaction is generally carried out in the temperature range from 0° to 120° C. If A is bromine, the preferred reagent is phosphorus tribromide or phosphorus pentabromide and the reaction is carried out in the temperature range from 0° to 50° C. If A is one of the groups —OCO—R or OSO$_2$—R, then the reagent will normally be the corresponding acid halide, in particular acid chloride. In this case, it is expedient to carry out the reaction in the temperature range from −20° to +50° C., with the preferred range being from −10° to +30° C., and in the presence of a weak base such as pyridine or triethylamine.

A suitable base is used for the removal of the hydrogenated leaving group (H-A). Examples of such bases are: tertiary amines (triethylamine, ethyl diisopropylamine etc.); bicyclic amines such as 1,4-diazabicyclo[2.2.2]octane, 1,5-diazabicyclo[3.4.0]non-5-ene etc.; anilines such as N,N-dimethylaniline, N,N-methylethylaniline etc.; heterocyclic bases such as pyridine, collidine, quinoline etc.; and also inorganic bases such as sodium acetate, sodium bicarbonate, alkali metal hydroxides and alkaline earth metal hydroxides [NaOH, KOH, Ca(OH$_2$), Ba(OH)$_2$]; alkali alcoholates (sodium or potassium ethanolate, potassium tert-butylate). The reaction is carried out in the temperature range from 0° to 120° C.

(iii) Another process variant for obtaining compounds of the formula I comprises starting from chloro-olefin derivatives of the formula VII

 (VII)

wherein R$_2$ and R$_3$ are as defined for formula I, Hal is halogen, preferably fluorine, chlorine or bromine, and reacting these in the melt in the temperature range from 150° to 350° C. and optionally under pressure, with an excess of azole of the formula VIII

 (VIII)

wherein R$_1$ is an azole group. In this reaction, up to a ten-fold excess of azole of the formula VIII is employed, preferably a three-fold excess, based on the compound of formula VII.

(iv) In a further process, compounds of the formula I can be obtained from compounds of the formula IX

 (IX)

wherein R$_2$ and R$_3$ are as defined for formula I, and Hal is halogen, preferably fluorine, chlorine or bromine, by reacting these in a dipolar aprotic solvent, if desired in the presence of a base, in the temperature range from 40° to 180° C., preferably from 80° to 120° C., or in the melt in the temperature range from 150° to 350° C., with an excess of azole of the formula VIII.

The base can be added to the reaction mixture in the course of the melt procedure. If necessary, the process is carried out under pressure (up to 15 bar). Suitable bases are, in particular, inorganic bases such as alkali metal hydroxides and alkaline earth metal hydroxides (NaOH, KOH). Examples of suitable aprotic solvents are dimethylformamide, dimethylsulfoxide, hexamethylphosphoric triamide, and nitriles such as acetonitrile.

Some of the starting compounds of the formula II are known and commercially available, or they may be readily obtained by methods corresponding to those employed for obtaining the known compounds.

The 1H-azol-1-ylmethylphosphonates of the formula III can be prepared by reacting a 1-halomethyl-1H-azole of the formula X

 (X), wherein Hal is chlorine, bromine or iodine, either with a secondary phosphite of the formula XI

 (XI)

wherein each $R_{10}$ independently of the other is phenyl or $C_1$-$C_4$alkyl and M is an alkali metal atom, or with a tertiary phosphite of the formula XII

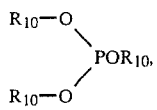 (XII)

wherein $R_{10}$ is as defined for formula XI.

The process for the production of the phosphonates of the formula III is conveniently carried out in an inert organic solvent. Such solvents are aromatic hydrocarbons such as benzene, toluene or xylene; ethers such as diethyl ether, tetrahydrofuran, dioxan, dimethoxyethane, or diethylene glycol dimethyl ether; or nitriles such as acetonitrile.

If a secondary alkali phosphite of the formula XI is used, it is expedient to use a polar solvent such as acetonitrile, dimethoxyethane or diethylene glycol dimethyl ether. If a tertiary phosphite of the formula VII is used for the synthesis of the phosphonates, then this itself can often be used as solvent.

At all events, however, it is advisable to heat the reaction mixture: in the reaction with the secondary phosphite to 50°–150° C., preferably 80°–120° C., and in the reaction with the tertiary phosphite, to 100°–180° C., preferably 120°–160° C.

The secondary alkali phosphites are in general sodium or potassium phosphites.

The phosphites of the formula III are isolated by removing any precipitate formed, evaporating the solution and distilling the residue.

The 1H-azol-1-ylmethylphosphonium salts of the general formula IV can be prepared by reacting a 1-halomethyl-1H-azole of the formula X with a phosphine of the formula XIII

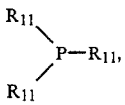 (XIII)

wherein $R_{11}$ is as defined for formula IV.

The process for obtaining the phosphonium salts of the formula IV is conveniently carried out in an inert organic solvent. Such solvents are aromatic hydrocarbons such as benzene, toluene or xylene; ethers such as diethyl ether, tetrahydrofuran, dioxan, dimethoxyethane or diethylene glycol dimethyl ether; acid amides such as dimethylformamide or 2-pyrrolidinone; or nitriles such as acetonitrile. It is preferred to use polar solvents such as dimethyl formamide, acetonitrile or dimethoxyethane.

It is advisable to heat the reaction mixture to 30°–120° C., preferably to 50°–100° C.

The phosphonium salts usually crystallise out from the cooled reaction mixtures, so that in general it is not necessary to isolate these compounds by extraction or precipitation procedures. If the product does not precipitate directly, it can be obtained by simple evaporation of the solvent.

A number of the phosphonium salts of the formula IV also have themselves fungicidal properties and, where novel, constitute an object of the invention.

The 1-halomethyl-1H-azoles of the fomula X $Hal—CH_2—R_1$ (X), wherein Hal is chlorine, bromine or iodine, are obtained by reacting a 1-hydroxymethyl-1H-azole of the formula XIV $HO—CH_2—R_1$ (XIV)

with a halogenating agent, and treating the resultant hydrohalide of the formula XV $Hal—CH_2—R_1.HHal$ (XV), wherein Hal is as defined for formula X, with a base.

Suitable bases are strong inorganic hydroxides such as sodium hydroxide and potassium hydroxide.

Suitable halogenating agents are: phosgene, thionyl chloride, thionyl bromide, phosphorus trichloride, phosphorus tribromide, phosphorus pentachloride, phosphoroxy chloride or hydriodic acid. Preferred halogenating agents are thionyl chloride and thionyl bromide, as the by-products formed are gaseous, escape from the reaction solution, and therefore do not influence the reaction. The iodo compounds are conveniently obtained from already halogenated compounds by reacting these latter with hydriodic acid.

A further method of obtaining corresponding chlorides, bromides and iodides comprises reacting compounds of the formula XIV with the corresponding trialkylsilyl halides.

The halogenation reaction is carried out in an inert solvent, e.g. a hydrocarbon such as hexane, cyclohexane, benzene, toluene or xylene, or an ether such as diethyl ether, tetrahydrofuran, dioxan or dimethoxyethane. When using a liquid halogenating agent, it is frequently possible to dispense with a solvent entirely. The reaction is then carried out in an excess of reagent, e.g. thionyl chloride or thionyl bromide.

Unless otherwise expressly specified, one or more inert solvents or diluents may be present in the preparation of all starting materials, intermediates and final products mentioned herein. Examples of suitable inert solvents or diluents are: aliphatic and aromatic hydrocarbons such as benzene, toluene, xylenes, petroleum ether; halogenated hydrocarbons such as chlorobenzene, methylene chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxan, tetrahydrofuran; nitriles such as acetonitrile, propionitrile; N,N-dialkylated amides such as dimethylformamide; dimethylsulfoxide; ketones such as acetone, diethyl ketone, methyl ethyl ketone; and mixtures of such solvents with each other. It can often be convenient to carry out the reaction, or partial steps of a reaction, under an inert gas atmosphere and/or in absolute solvents. Suitable inert gases are nitrogen, helium, argon or, in certain cases, also carbon dioxide. Carrying out the reaction under pressure can also favourably influence the yields.

Most of the starting materials of the formula V are known or they can be prepared by methods analogous to those described in the art (q.v. GB patent specification No. 2 064 520).

Compounds of the type of formula VII are also disclosed in European patent specification No. 0 004 315, or they can be prepared by the methods described therein. Compounds of the type of formula IX are also known from the literature or may be prepared by methods similar to known ones (q.v. JACS 67, 1591 (1945)]. The starting compounds of the formulae VIII, XI, XII, XIII and XIV are generally known, constitute in general basic chemicals and can be prepared by methods known per se. Most of them are commercially availabe.

Surprisingly, it has now been found that the novel compounds of the formula I and compositions containing them are characterised in particular by their selective influence on plant metabolism. This selective inluence on the physiological processes of plant development makes it possible to use the compounds of formula I for different purposes, especially for those in connection with increasing the yield of useful plants, with facilitating harvesting, and with labour-saving in measures taken in crops of cultivated plants.

Previous experience with the application of growth regulators has shown that the active ingredients can induce one or more different responses in the plants. These different responses depend largely on the time of application, based on the development state of the seed or plant, as well as on the concentrations of active ingredient applied to the plants or the locus thereof. Growth regulators should at all events induce positive responses in the cultivated plants in the desired manner.

Growth regulators may be used e.g. for inhibiting vegetative plant growth. Such a growth inhibition is of economic interest, inter alia, in respect of grasses, as the frequency of cutting in flower gardens, parks, sports fields or road shoulders can thereby be reduced. Of importance too is the inhibition of growth of herbaceous and ligneous plants on road shoulders and near transmission lines, or generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whilst vegetative growth is inhibited.

Growth regulators are also frequently able to promote vegetative growth. This is of great value when the vegetative parts of plants are to be harvested. However, promotion of vegetative growth can also result simultaneously in promotion of generative growth, so that e.g. more or larger fruit is formed.

Yield increases may also often be obtained by influencing the plant metabolism without any visible changes in vegetative growth. Growth regulators can also induce a change in the composition of plants, so that the quality of the harvest product is improved. For example, it is possible to increase the sugar content of sugar beet, sugar cane, pineapples and citrus fruit, or to increase the protein content of soya beans or cereals.

The use of growth regulators can lead to the formation of parthenocarpic fruit. The sex of blossoms can also be influenced. The production or flow of secondary plant substances can also be positively influenced by growth regulators, for example the stimulation of the flow of latex in rubber trees.

During plant growth, the development of side-shoots can also be promoted by the chemical interruption of apical dominance using growth regulators. This is of interest e.g. in the propagation of plant cuttings. However, it is also possible to inhibit the growth of side-shoots, e.g. in tobacco plants after decapitation in order to prevent the formation of side-shoots and thus to promote leaf growth.

Premature fruit drop can be prevented by the use of growth regulators. However, it is also possible to promote fruit drop—e.g. in fruit crops—by means of chemical thinning up to a specific degree. Growth regulators can also be used for reducing the force necessary for detaching fruit at harvesting, thus making possible mechanical harvesting of plants or facilitating manual harvesting.

With growth regulators it is also possible to speed up or delay the ripening of harvest products before or after harvesting. This is particularly advantageous, because a best possible accomodation to market requirements can thereby be achieved. In addition, growth regulators can often improve the colour of fruit. With the aid of growth regulators it is also possible to concentrate ripening at a particular time. The conditions are thus created for a complete mechanical harvesting of e.g. tobacco, tomatoes or coffee, or for manual harvesting, in only one single operation.

The application of growth regulators can also make it possible to influence the dormancy of seeds and buds of plants, i.e. the endogenic annual rhythm, so that plants such as pineapples or ornamentals in nurseries germinate, sprout or blossom at a time when they would normally not tend to do so.

With growth regulators it is also possible to delay budding or the germination of seeds, e.g. in order to avoid damage by late frosts in areas endangered thereby. Conversely, root growth and/or the formation of shoots can be stimulated, so that growth may be restricted to a shorter period.

Growth regulators can also impart halophilic properties to cultivated plants. The conditions are thus created for cultivating plants in salty soil. Growth regulators can also impart to plants resistance to frost and drought.

Under the influence of growth regulators, the ageing (senescence) of plants or parts of plants can be inhibited or delayed. Such an action can be of great economic importance, as the storability of treated parts of plants or whole plants such as fruit, berries, vegetables, salads or ornamentals can be improved or prolonged after harvesting. Likewise, a substantial yield increase can be obtained by treating cultivated plants by prolonging the phase of photosynthetic activity.

A further important field of use for growth regulators is the inhibition of excessive growth of tropical cover crops. In tropical and subtropical monocultures, e.g. in palm tree plantations, cotton and maize fields etc., cover crops, especially species of leguminosae, are often planted with the object of maintaining or improving the quality of the soil (prevention of desiccation, supplying nitrogen) and for preventing erosion. By applying the compounds of this invention it is possible to control the growth of these cover crops and so to keep the growth in height of these plants at a low level, thus ensuring healthy growth of the cultivated plants and the maintenance of favourable soil conditions. Surprisingly, it has also been found that, in addition to their advantageous growth regulating properties, the compounds of formula I and the compositions containing them also have for practical purposes a very useful microbicidal spectrum. A further field of use of the compounds of formula I is therefore the control of harmful microorganisms, especially phytopathogenic fungi. The compounds of formula thus have for practical purposes a very useful curative, preventive and systemic action for protecting plants, especially cultivated plants, without adversely affecting them. With the compounds of formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Ascomycetes (e.g. Venturia, Podosphaera, Erysiphe, Monilinia, Uncinula); Basidomycetes (e.g. the genera Hemileia, Rhizoctonia, Puccinia); Fungi imperfecti (e.g. Botrytis, Helminthosporium, Fusarium, Septoria, Cercospora and Alternaria). In addition, the compounds of formula I have a systemic action. They can also be used as seed dressing agents for protecting seeds (fruit, tubers, grains) and plant cuttings against fungus infections as well as against phytopathogenic microorganisms which occur in the soil.

The compounds of the invention are especially well tolerated by plants.

Accordingly, the invention also relates to microbicidal compositions and to the use of compounds of the formula I for controlling phytopathogenic microorganisms, especially harmful fungi, and for the preventive treatment of plants to protect them from attack by such microorganisms. The invention further relates to the preparation of agrochemical compositions, which comprises homogeneously mixing the active ingredient with one or more compounds or groups of compounds described herein. The invention furthermore relates to a method of treating plants, which comprises applying thereto the compounds of the formula I or the novel compositions.

Target crops to be protected within the scope of the present invention comprise e.g. the following species of plants: cereals (wheat, barley, rye, oats, rice, sorghum and related crops); beet (sugar beet and fodder beet); drupes, pomes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconuts, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, luttuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (composites), areas of grass, embankments or general low cover crops which counteract erosion or desication of the soil and are useful in cultures of trees and perennials (fruit plantations, hop plantations, maize fields, vineyards etc.).

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these compositions, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilisers.

A preferred method of applying a compound of the formula I or an agrochemical composition which contains at least one of said compounds, is foliar application. The number of applications and the rate of application depend on the intensity of infestation by the corresponding pathogen (type of fungus) or on the manner in which growth is influenced. However, the compounds of formula I can also penetrate the plant through the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of the formula I, or by coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances. Advantageous rates of application are normally from 10 g to 5 kg of active ingredient (a.i.) per hectare, preferably from 100 g to 2 kg a.i./ha, most preferably from 200 g to 600 g a.i./ha. The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues. Phospholipids are particularly preferred.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Inc. New York, 1980.

The agrochemical compositions usually contain 0.1 to 99%, preferably 0.1 to 95%, of a compound of the formula I, 99.9 to 1%, preferably 99.8 to 5%, of a solid or liquid adjuvant, and 0 to 25%, preferably 0.1 to 25%, or a surfactant. Whereas commercial products are preferably formulated as concentrates, the end user will normally employ dilute formulations.

The compositions may also contain further ingredients, such as stabilisers, antifoams, viscotity regulators, binders, tackifiers as well as fertilisers or other active ingredients in order to obtain special effects.

Such agrochemical compositions also constitute an object of the present invention.

The invention is illustrated in more detail by the following Examples, without implying any restriction to what is described therein. Parts and percentages are by weight.

PREPARATORY EXAMPLES FOR THE STARTING MATERIALS

Example A

Preparation of

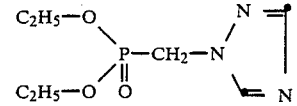

diethyl (1H-1,2,4-triazol-1-yl)methylphosphonate (a) 11.7 g (0.1 mole) of freshly prepared 1-chloromethyl-1H-1,2,4-triazole are added dropwise at 90° C. to a dispersion of 17.6 g (0.1 mole) of potassium diethyl phosphite in 100 ml of toluene. When the exothermic reaction is complete, the precipitated potassium chloride is removed and the filtrate is concentrated. The residue is chromatographed with ethyl acetate over silica gel, giving 2.1 g (9.6%) of a yellow oil. Distillation of this oil in a bulb tube gives diethyl (1H-1,2,4-triazol-1-yl)methylphosphonate in the form of a colourless oil with a boiling point of 130° C./0.11 mb.

$^1$H-NMR (CDCl$_3$, TMS): $\delta$ = 8.4 (s; 1H, triazole 5-CH); 8.07 (s; 1H, triazole 3-CH); 4.75 (d, $J_{PCH}$=13 Hz; 2H, P-CH$_2$); 4.25 (2q, J=7 Hz; 4H, OCH$_2$) and 1.5 (t, J=Hz; 6H, CH$_3$) ppm.

$^{31}$P-NMR (CD$_3$OD, H$_3$PO$_4$): $\delta$ = +17.12 ppm.

(b) A mixture of 18.2 g (0.155 mole) of 1-chloromethyl-1H-1,2,4-triazole, 27.2 g (0.17 mole) of sodium diethyl phosphite and 200 ml of acetonitrile is heated for 2 hours to 60° C. and then refluxed for 16 hours. The precipitate is removed and the solution is concentrated.

Fractional distillation of the residue yields 19.1 g (56.5%) of diethyl (1H-1,2,4-triazol-1-yl)methylphosphonate in the form of a colourless oil with a boiling point of 120°–129° C./0.053 mb.

$C_7H_{14}N_3O_3P$ (219.2): cal.: C 38.36%; H 6.44%; N 19.17%; found: C 38.37%; H 6.60%; N 19.76%.

PREPARATORY EXAMPLES FOR THE FINAL PRODUCTS

Example 1

Preparation of

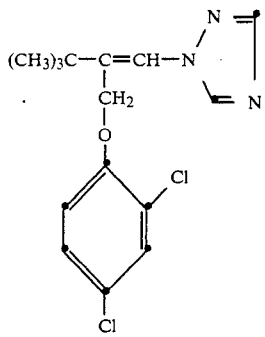

1-(1H-1,2,4-triazol-1-yl)-2-(2,4-dichlorophenoxymethyl)-3,3-dimethylbutene

With stirring, 100 ml of dichloromethane and 10 ml of thionyl chloride are cooled to −30° C. and then 17.5 g (0.05 mole) of 1-(1H-1,3,4-triazolyl)-2-(2,4-dichlorophenoxymethyl)-3,3-dimethylbutanol are added in portions. The reaction mixture is stirred for 2 hours and then a solution of 15 ml of pyridine in 30 ml of dichloromethane is added dropwise and the mixture is stirred for about 12 hours at room temperature. The clear solution is concentrated in vacuo and, after addition of ice, the residue is made alkaline with sodium carbonate and extracted with diethyl ether. The combined extracts are dried over sodium sulfate, filtered and concentrated. The yellowish oily residue is purified by column chromatography over silica gel with ethyl acetate as eluant. Yield: 75% of theory.

Example 2

Preparation of

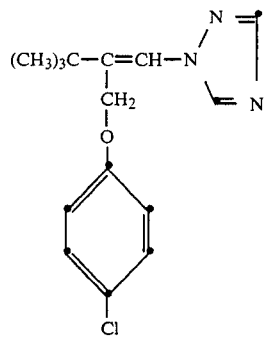

1-(1H-1,2,4-triazol-1-yl)-2-(4-chlorophenoxymethyl)-3,3-dimethylbutene 15 g of sodium hydride in the form of a 55% dispersion in oil are added under nitrogen to 150 ml of 1,2-dimethoxyethane. Then a solution of 69 g (0.315 mole) of diethyl (1H-1,2,4-triazol-1-yl)methylphosphonate, 68 g (0.3 mole) of 2,2-dimethyl-4-(4-chlorophenoxy)butan-3-one and a trace of 15-crown-5 in 500 ml of dimethoxyethane are added dropwise. The reaction mixture is stirred for about 10 hours and, after the dropwise addition of ice/water, extracted with methylene chloride. The combined extracts are washed with water, dried over sodium sulfate, filtered and concentrated. The oily residue is purified by column chromatography over silica gel with a 4:2:2:2 mixture of toluene/cyclohexane/diethyl ether/dichloromethane as eluant, affording the product in the form of a yellow oil.

$^1$H-NMR (CDCl$_3$, TMS): δ=8.4 (s; 1H triazole 5-CH); 8.0 (s; 1H, triazole 3-CH); 7.4–6.8 (m; 5H, aryl C—H and olefin C—H); 4.5 (s; 2H, CH$_2$—O); 1.2 (s, 9H, tert-butyl).

The following compounds of the formula I as well as the indicated intermediates are prepared in corresponding manner. Unless specifically mentioned, the product is obtained in the form of a mixture of E- and Z-isomers, so that the physical data relate to the mixture of isomers.

TABLE 1

Compounds of the formula

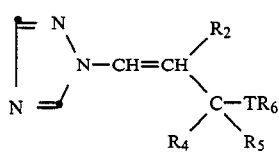

| Compound | R$_2$ | R$_4$ | R$_5$ | R$_6$ | T | Physical data (°C.) |
|---|---|---|---|---|---|---|
| 1.1 | C$_4$H$_9$—t | H | H | C$_6$H$_4$Cl(4) | O | mixture of isomers: oil; E-isomer m.p. 48–50°; Z-isomer m.p. 82–86° |
| 1.2 | C$_4$H$_9$—t | H | H | C$_6$H$_3$Cl$_2$(2,4) | O | oil |
| 1.3 | C$_4$H$_9$—t | H | H | C$_6$H$_4$F(4) | O | mixture of isomers: resin; E-isomer m.p. 68–70°; Z-isomer m.p. 79–81° |
| 1.4 | C$_4$H$_9$—t | H | H | C$_6$H$_4$CF$_3$(3) | O | |
| 1.5 | C$_4$H$_9$—t | H | H | C$_6$H$_3$Cl(2)Br(4) | O | |
| 1.6 | C$_4$H$_9$—t | H | H | C$_6$H$_5$ | O | |
| 1.7 | C$_4$H$_9$—t | H | H | β-naphthyl | O | |
| 1.8 | C$_4$H$_9$—t | H | H | 4-biphenyl | O | |

TABLE 1-continued

Compounds of the formula $$\text{[pyrimidinyl]}-N(-CH=CH)-\underset{R_4 \;\; R_5}{C(R_2)}-C-TR_6$$

| | $R_2$ | | | $R_6$ | T | Physical data |
|---|---|---|---|---|---|---|
| 1.9 | $C_4H_9-t$ | H | H | 4-benzylphenyl | O | |
| 1.10 | $C_4H_9-t$ | H | H | 4-phenoxyphenyl | O | |
| 1.11 | $C_4H_9-t$ | H | H | 4-benzyloxyphenyl | O | |
| 1.12 | $C_4H_9-t$ | H | H | $C_6H_4Cl(4)$ | S | |
| 1.13 | $C_5H_{11}-n$ | H | H | $C_6H_4Cl(4)$ | O | $n_D^{25} = 1.5428$ |
| 1.14 | $C_4H_9-t$ | H | H | $C_6H_4F(4)$ | O | m.p. 68–70° |
| 1.15 | $CH_3$ | H | H | $CH_3$ | O | oil |
| 1.16 | $CH_3$ | H | H | biphenyl | O | |
| 1.17 | $CH_3$ | H | H | $C_6H_3Cl(2)Br(4)$ | O | |
| 1.18 | $C(CH_3)_2H$ | H | $C_2H_5$ | $C_6H_4Cl(4)$ | O | $n_D^{25} = 1.5418$ |
| 1.19 | $C_4H_9-t$ | H | $C_2H_5$ | $C_6H_4Cl(4)$ | O | $n_D^{35} = 1.5360$ |
| 1.20 | $C_4H_9-t$ | H | $C_3H_7-n$ | $C_6H_4Cl(4)$ | O | $n_D^{35} = 1.5335$ |
| 1.21 | $C_4H_9-t$ | H | $C_4H_9-n$ | $C_6H_4Cl(4)$ | O | $n_D^{35} = 1.5190$ |
| 1.22 | $C(CH_3)_2H$ | H | $C_3H_7-n$ | $C_6H_4Cl(4)$ | O | $n_D^{35} = 1.5388$ |
| 1.23 | $C(CH_3)_2H$ | H | $CH_3$ | $C_6H_4Cl(4)$ | O | $n_D^{35} = 1.5460$ |
| 1.24 | $C(CH_3)_2H$ | H | $C_2H_5$ | $C_6H_4CH_3(4)$ | O | $n_D^{35} = 1.5288$ |
| 1.25 | $(CH_2)_8CH_3$ | H | $C_2H_5$ | $C_6H_4Cl(4)$ | O | $n_D^{36} = 1.5170$ |
| 1.26 | $C_4H_9-t$ | H | $CH_3$ | $C_6H_4F(4)$ | O | $n_D^{36} = 1.5191$ |
| 1.27 | $C_4H_9-t$ | H | $CH_3$ | $C_6H_4Cl(4)$ | O | $n_D^{36} = 1.5410$ |
| 1.28 | $C(CH_3)_2H$ | H | $C_2H_5$ | $C_6H_3CH_3(2)Cl(4)$ | O | $n_D^{36} = 1.5289$ |
| 1.29 | $(CH_2)_4CH_3$ | H | $C_2H_5$ | $C_6H_4Cl(4)$ | O | $n_D^{36} = 1.5261$ |
| 1.30 | $C_4H_9-t$ | H | $C_2H_5$ | $C_6H_4F(4)$ | O | $n_D^{36} = 1.5088$ |
| 1.31 | $C(CH_3)_2H$ | H | $C_2H_5$ | $C_6H_4Br(4)$ | O | $n_D^{36} = 1.5502$ |
| 1.32 | $C_4H_9-t$ | H | $C_2H_5$ | $C_6H_4CF_3(4)$ | O | $n_D^{37} = 1.4940$ |
| 1.33 | $C_4H_9-t$ | H | $C_2H_5$ | $C_6H_4Cl(2)$ | O | $n_D^{36} = 1.5370$ |
| 1.34 | $CH_2CH(CH_3)_2$ | H | $C_2H_5$ | $C_6H_9Cl(4)$ | O | b.p. 155°/5.10$^{-3}$ mbar |
| 1.35 | cyclopropyl-$CH_3$ | H | H | $C_6H_4Cl(4)$ | O | |
| 1.36 | cyclopropyl-$CH_3$ | H | H | $C_6H_3Cl_2(2,4)$ | O | |
| 1.37 | $C_6H_3Cl_2(2,4)C(CH_3)_2$ | H | H | $C_6H_5$ | O | |
| 1.38 | $C_6H_3Cl_2(2,4)C(CH_3)_2$ | H | H | $C_6H_4F(4)$ | O | |
| 1.39 | $C_6H_3Cl_2(2,4)C(CH_3)_2$ | H | H | $C_6H_4Cl(4)$ | O | |

| Compound | $R_2$ | $R_4$ = | $R_5$ | $R_6$ | T | Physical data |
|---|---|---|---|---|---|---|
| 1.140 | $C_4H_9-t$ | | $CH_3$ | 4-Cl-phenyl | O | |
| 1.141 | $C_4H_9-t$ | | $CH_3$ | $C_6H_4Cl(4)$ | O | |
| 1.142 | 2,4-Cl$_2$-phenyl-C(CH$_3$)$_2$ | | H | 2-CH$_3$-4-CH$_3$-phenyl | | — |
| 1.143 | $CH_3$ | | H | $-CH_2CH=CH_2$ | | — |
| 1.144 | $CH_3$ | | H | $-C(CH_3)_2-COOCH_3$ | | — |
| 1.145 | $CH_3$ | | H | $-CH_2CH_2C=C(CH_3)_2$ | | — |

TABLE 1-continued

Compounds of the formula

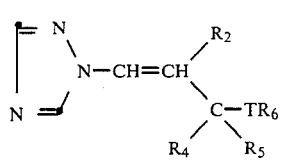

| | | | | | |
|---|---|---|---|---|---|
| 1.146 | CH₃ | H | —CH—CH₂OCH₃—<br>    \|<br>    CH₃ | — | |
| 1.147 | CH₃ | H |         CH₃<br>        \|<br>—CH₂—CH—OC₂H₅ | — | |
| 1.148 | (CH₃)₃C— | H |  | — | |
| 1.149 | (CH₃)₃C— | H | 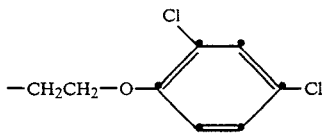 | — | |
| 1.150 | (CH₃)₃C— | H |  | — | |
| 1.151 | (CH₃)₃C— | H | —CH₂CH₂OC₂H₅ | — | |
| 1.152 | C(CH₃)₂H | H | C₆H₄Cl(4) | O | $n_D^{25} = 1.5501$ |
| 1.153 | C(CH₃)₂H | H | C₆H₄F(4) | O | |
| 1.154 | C(CH₃)₂H | H | C₆H₄Br(4) | O | |
| 1.155 | C(CH₃)₂H | H | C₆H₄CH₃(4) | O | |
| 1.156 | C(CH₃)₂CH₂CH₃ | H | C₆H₄Cl(4) | O | |
| 1.157 | C(CH₃)₂CH₂CH₃ | H | C₆H₄F(4) | O | |
| 1.158 | C(CH₃)₂CH₂CH₃ | H | C₆H₄Br(4) | O | |
| 1.159 | C(CH₃)₂CH₂CH₂ | H | C₆H₄CH₃(4) | O | |
| 1.160 | C(CH₃)HCH₂CH₂CH₃ | H | C₆H₄Cl(4) | O | $n_D^{25} = 1.5459$ |
| 1.161 | C(C₂H₅)HC₄H₉—n | H | C₆H₄Cl(4) | O | b.p. 155–160°/<br>0.002 mbar |
| 1.162 | C(C₂H₅)HC₄H₉—n | H | C₆H₄CH₃(4) | O | b.p. 150–155°/<br>0.004 mbar |
| 1.163 | C(CH₃)HCH₂CH₃ | H | C₆H₄CH₃(4) | O | |
| 1.164 | C(CH₃)HCH₂CH₃ | H | C₆H₃Cl₂(2,4) | O | |
| 1.165 | C(CH₃)₂CH₂CH₃ | H | C₆H₃Cl₂(2,4) | O | |
| 1.166 | C(CH₃)₂H | H | C₆H₃Cl₂(2,4) | S | |
| 1.167 | C(CH₃)₂H | H | C₆H₃Cl₂(2,4) | O | |
| 1.168 | C(CH₃)₂H | CH₃ | C₆HF(4) | O | |

FORMULATION EXAMPLES

Formulation Examples for liquid active ingredients of the formula I (throughout, percentages are by weight)

3. Emulsifiable concentrates

| | (a) | (b) | (c) |
|---|---|---|---|
| a compound of table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether - (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

4. Solutions

| | (a) | (b) | (c) | (d) |
|---|---|---|---|---|
| a compound of table 1 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| 5. Granulates | (a) | (b) |
|---|---|---|
| a compound of table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently stripped off in vacuo.

| 6. Dusts | (a) | (b) |
|---|---|---|
| a compound of table 1 | 2% | 5% |
| highly dispersed silicic acid | 1% | 5% |
| talcum | 97% | — |
| kaolin | — | 90% |

Ready-to-use dusts are obtained by intimately mixing the carriers with the active ingredient.

Formulation examples for solid active ingredients of the formula I (throughout, percentages are by weight)

| 7. Wettable powders | (a) | (b) | (c) |
|---|---|---|---|
| a compound of table 1 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 8. Emulsifiable concentrate | |
|---|---|
| a compound of table 1 | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 9. Dusts | (a) | (b) |
|---|---|---|
| a compound of table 1 | 5% | 8% |
| talcum | 95% | — |
| kaolin | — | 92% |

Ready-for-use dusts are obtained by mixing the active ingredient with the carriers, and grinding the mixture in a suitable mill.

| 10. Extruder granulate | |
|---|---|
| a compound of table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 11. Coated granulate | |
|---|---|
| a compound of table 1 | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 12. Suspension concentrate | |
|---|---|
| a compound of table 1 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example 13

Action against Puccinia graminis on wheat (a) Residual-protective action

Wheat plants are treated 6 days after sowing with a spray mixture prepared from a wettable powder formulation of the test compound (0.06%). After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture prepared from a wettable powder formulation of the test compound (0.006%, based on the volume of the soil). After 48 hours the treated plants are infected with a uredospore suspension of the fungus. The plants are then incubated for 48 hours at 95–100% relative humidity and about 20° C. and then stood in a greenhouse at about 22° C. Evaluation of rust pustule development is made 12 days after infection. Compounds of Table 1 are effective against Puccinia fungi. Puccinia attack is 100% on untreated and infected control plants. In particular, compounds of claim 3 have pronounced activity against Puccinia fungi, especially compound 1.1.

Example 14

Action against Cercospora arachidicola in groundnut plants

Residual protective action

Groundnut plants 10–15 cm in height are sprayed with a spray mixture (0.02%) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected controls (number and size of the specks=100%), Cercospora attack on groundnut plants treated with compounds of Table 1 is greatly reduced. Thus the compounds of claim 3 inhibit Cercospora attack. Compound 1.1 reduces attack very substantially, viz. to 0–5%.

Example 15

Action against Erysiphe graminis on barley (a) Residual protective action

Barley plants about 8 cm in height are sprayed with a spray mixture (0.02%) prepared from the test compound formulated as a wettable powder. The treated plants are dusted with conidia of the fungus after 3–4 hours. The infected barley plants are then stood in a greenhouse at about 22° C. The extent of the infestation is evaluated after 10 days.

(b) Systemic action

Barley plants about 8 cm in height are treated with a spray mixture (0.006%) based on the volume of the soil) prepared from the test compound formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and evaluation of infestation is made after 10 days.

Compounds of the formula I are very effective against Erysiphe fungi. Erysiphe attack is 100% on untreated and infected control plants. Among other compounds of Table 1, compounds 1.1 and 1.2 and also other representatives, especially the compounds of claim 3, are particularly effective against Erysiphe fungi.

Example 16

Residual-protective action against Venturia inaequalis on apple shoots

Apple cuttings with 10–20 cm long fresh shoots are sprayed with a spray mixture (0.06%) prepared from a wettable powder formulation of the active ingredient. The plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection.

Compounds of claim 3 are particularly effective against Venturia fungi.

Example 17

Action against Botrytis cinerea on beans

Residual protective action

Bean plants about 10 cm in height are sprayed with a spray mixture (0.02%) prepared from the test compound formulated as wettable powder. After 48 hours, the treated plants are infected with a conidia suspension of the fungus. The infected plants are incubated for 3 days at 95–100% relative humidity and 21° C., and evaluation of the fungus attack is then made. Many compounds of Table 1 very strongly inhibit fungus attack. At a concentration of 0.02% compounds 1.1, 1.2 and further representatives of claim 3 have pronounced activity against Botrytis fungi. Some inhibit attack completely.

Example 18

Growth inhibition of cereals

Summar barley (Hordeum vulgare) and summer rye (Secale) are sown in sterilised soil in plastic beakers in a greenhouse and watered as required. The cereal shoots are treated about 21 days after sowing with an aqueous spray mixture of a compound of the formula I. The concentration corresponds to 0.5 and 2.5 kg respectively of active ingredient per hectare. Evaluation of the growth of the cereals is made 10 and 21 days after application. A comparison with untreated controls shows that the growth of cereal plants treated with compounds of the formula I is reduced.

Example 19

Growth inhibition of grasses

Seeds of the grasses Lolium perenne, Poa pratensis, Festuca ovina, and Cynodon dactylon are sown in plastic dishes filled with an earth/peat/sand mixture (6:3:1), in a greenhouse, and watered as required. The emergent grasses are cut back weekly to a height of 4 cm and, about 50 days after sowing and 1 day after the last cut, are sprayed with an aqueous spray mixture of a compound of the formula I. The concentration of test compound corresponds to a rate of application of 0.5 and 2.5 kg per hectare respectively. The growth of the grasses is evaluated 10 and 21 days after application. The evaluation shows that the compounds of Table 1 effect a reduction in growth.

Example 20

Increase in yield of soybeans

Soybeans of the "Hark" variety are sown in plastic containers in an earth/peat/sand mixture (6:3:1). The containers are put into a climatic chamber and the plants develop to the 5–6 trefoil leaf stage after about 5 weeks by optimum control of temperature, light, fertiliser addition, and watering. The plants are then sprayed with an aqueous mixture of a compound of the formula I until thoroughly wetted. Evaluation is made about 5 weeks after application. Compared with untreated controls, the compounds of the formula I markedly increase the number and weight of the harvested siliques. The compounds of Table 1 are particularly effective. In particular compounds 1.1, 1.13, 1.14, 1.34, 1.60, 1.61 and 1.162 effect an increase in yield. Compound 1.21 is particularly effective.

Example 21

Growth inhibition of cover crops

Test plants of the varieties Psophocarpus palustris and Centrosema pubescens are reared from cuttings in plastic pots filled with an earth/turf/sand mixture (1:1:1). After they have grown roots, the plants are transplanted into 9 cm pots and watered as required. For further growth the plants are then kept in a greenhouse at a day temperature of 27° C. and a night temperature of 21° C. The average light exposure is 14 hours (6000 lux) and the humidity is 70%. The plants are cut back to a height of about 15 cm and sprayed 7 days later with a spray mixture of the test compound (Corresponding to a rate of application of 0.3 and 3 kg/a.i./ha respectively). Four weeks after application the growth of the plants is compared with that of untreated control plants which have been cut back. It is found that many compounds of Table 1 effect a marked growth inhibition of the cover plants.

Example 22

Inhibition of senescence in cereal plants

Summer wheat of the "Svenno" variety is sown in pots with compost soil and reared without special climatic conditions. About 10 days after emergence, 10 to 12 cm long primary leaves are cut off and put individually into test tubes containing 10 ml of suspension of test compound (1.25 to 10 ppm). The test tubes are kept in a climatic room at 23° C. and 70% relative humidity and irradiated daily for an average of 14 hours (10,000 lux). Evaluation of senescence is made 7 days later by comparing the degree of yellowing with still fresh, green leaves. This test shows that compounds of Table 1 markedly inhibit the senescence of the test plants. In particular, they inhibit yellowing of the leaves by more than 80% during the test period.

What is claimed is:

1. A compound of the formula

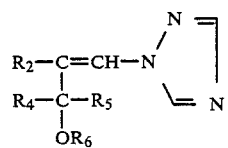

wherein
$R_2$ is $C_1$-$C_9$ alkyl;
$R_4$ and $R_5$ independently of the other are hydrogen or $C_1$-$C_4$ alkyl; and
$R_6$ is $C_1$-$C_3$ alkyl, phenyl or phenyl which is substituted by halogen, $CF_3$ or $C_1$-$C_3$ alkyl.

2. A compound according to claim 1, wherein $R_2$ is tert-butyl or isopropyl, $R_4$ is hydrogen, $R_5$ is $C_1$-$C_4$ alkyl, and $R_6$ is methyl, phenyl or phenyl which is substituted by chlorine, bromine, fluorine, $CF_3$ or methyl.

3. 1-(1H-1,2,4-triazol-1-yl)-2-(4-chlorophenoxymethyl)-3,3-dimethylbutene according to claim 2.

4. 1-(1H-1,2,4-triazol-1-yl)-2-(isopropyl)-3-(4-chlorophenoxy)pentene according to claim 2.

5. 1-(1H-1,2,4-triazol-1-yl)-2-(tert-butyl)-3-(4-chlorophenoxy)heptene according to claim 2.

6. 1-(1H-1,2,4-triazol-1-yl)-2-(tert-butyl)-3-(4-fluorophenoxy)butene according to claim 2.

7. A composition for controlling or preventing attack by fungi and/or for regulating plant growth, which composition contains as active ingredient an effective amount of a compound according to claim 1, together with an inert carrier.

8. A composition for controlling fungi which contains as active ingredient an effective amount of a compound according to claim 1 together with an inert carrier.

9. A method of controlling phytopathogenic fungi or of protecting cultivated plants from attack by said fungi, which method comprises applying to said plants or to the locus thereof a fungicidally effective amount of a compound of claim 1.

* * * * *